(12) United States Patent
Burck et al.

(10) Patent No.: US 9,676,799 B2
(45) Date of Patent: Jun. 13, 2017

(54) METHOD FOR THE SYNTHESIS OF N-(PHOSPHONOMETHYL)GLYCINE

(71) Applicant: STRAITMARK HOLDING AG, Zug (CH)

(72) Inventors: Sebastian Burck, Louvain-la-Neuve (BE); Frederic Bruyneel, Ophain-Bois-Sei-gneur-Isaac (BE); Patrick Notte, Wavre (BE)

(73) Assignee: STRAITMARK HOLDING AG, Zug (CH)

( * ) Notice: Subject to any disclaimer, the term of this patent is extended or adjusted under 35 U.S.C. 154(b) by 0 days.

(21) Appl. No.: 14/415,690

(22) PCT Filed: Jul. 17, 2013

(86) PCT No.: PCT/EP2013/065125
§ 371 (c)(1),
(2) Date: Jan. 19, 2015

(87) PCT Pub. No.: WO2014/012991
PCT Pub. Date: Jan. 23, 2014

(65) Prior Publication Data
US 2015/0175636 A1    Jun. 25, 2015

(30) Foreign Application Priority Data
Jul. 17, 2012  (EP) .................................... 12176756

(51) Int. Cl.
*A01N 57/20* (2006.01)
*C07F 9/38* (2006.01)
*C12P 13/04* (2006.01)

(52) U.S. Cl.
CPC ............ *C07F 9/3813* (2013.01); *A01N 57/20* (2013.01); *C12P 13/04* (2013.01)

(58) Field of Classification Search
CPC ......... A01N 57/20; C07F 9/3813; C12P 13/04
See application file for complete search history.

(56) References Cited

U.S. PATENT DOCUMENTS

| | | | |
|---|---|---|---|
| 3,288,846 A | 11/1966 | Irani et al. |
| 3,451,937 A | 6/1969 | Quimby |
| 3,455,675 A | 7/1969 | Irani et al. |
| 3,796,749 A | 3/1974 | Krueger et al. |
| 3,799,758 A | 3/1974 | Franz et al. |
| 3,816,517 A | 6/1974 | Krueger et al. |
| 3,832,393 A | 8/1974 | Krueger et al. |
| 3,927,080 A | 12/1975 | Gaertner |
| 3,969,398 A | 7/1976 | Hershman |
| 4,065,491 A | 12/1977 | Pfliegel et al. |
| 4,211,547 A | 7/1980 | Gaertner |
| 4,237,065 A | 12/1980 | Ehrat |
| 4,400,330 A | 8/1983 | Wong et al. |
| 4,422,982 A | 12/1983 | Subramanian |
| 4,617,415 A | 10/1986 | Balthazor et al. |
| 4,624,937 A | 11/1986 | Chou |
| 4,654,429 A | 3/1987 | Balthazor et al. |
| 4,657,705 A | 4/1987 | Miller et al. |
| 4,804,499 A | 2/1989 | Miller et al. |
| 4,931,585 A | 6/1990 | Pelyva et al. |
| 5,155,257 A | 10/1992 | Kleiner |
| 5,312,972 A | 5/1994 | Cullen |
| 5,312,973 A | 5/1994 | Donadello |
| 5,688,994 A | 11/1997 | Baysdon et al. |
| 7,084,298 B2 | 8/2006 | Maase et al. |
| 9,150,599 B2 | 10/2015 | Burck et al. |
| 2004/0024180 A1 | 2/2004 | Drauz et al. |
| 2015/0166584 A1 | 6/2015 | Devaux et al. |
| 2015/0232493 A1 | 8/2015 | Notte et al. |

FOREIGN PATENT DOCUMENTS

| | | |
|---|---|---|
| CA | 1039739 | 10/1978 |
| CH | 275435 | 5/1951 |
| CH | 620223 | 11/1980 |
| CN | 1631894 | 6/2005 |
| CN | 1285600 | 11/2006 |
| DE | 3903715 | 8/1989 |
| DE | 3903716 | 8/1989 |
| DE | 4026026 | 2/1992 |
| DE | 19909200 | 3/2000 |
| DE | 19914375 | 10/2000 |
| EP | 0480307 | 4/1992 |

(Continued)

OTHER PUBLICATIONS

Arizpe et al. Eur. J. Org. Chem. 2011, p. 3074-3081, "Stereodivergent synthesis of two a-aminophosphonic acids characterized by a cis-fused octahydroindole system."

(Continued)

*Primary Examiner* — Paul A Zucker
*Assistant Examiner* — Mark Luderer
(74) *Attorney, Agent, or Firm* — Brooks Kushman P.C.

(57) ABSTRACT

A method for the synthesis of N-(phosphonomethyl)glycine or one of its derivatives selected from the group consisting of its salts, its phosphonate esters, or its phosphonate ester salts, which includes the steps of: a) forming, in the presence an acid catalyst, a reaction mixture having 2,5-diketopiperazine, formaldehyde and a compound including one or more P-O-P anhydride moieties, the moieties having one P atom at the oxidation state (+III) and the other P atom at the oxidation state (+III) or (+V), to form N,N'-bisphosphonomethyl-2,5-diketopiperazine, its mono- to tetra phosphonate esters, the dehydrated forms of N,N'-bisphosphonomethyl-2,5-diketopiperazine and the phosphonate esters of its dehydrated forms; and b) hydrolyzing the N,N'-bisphosphonomethyl-2,5-diketopiperazine, its dehydrated forms or their phosphonate esters to obtain N-(phosphonomethyl)glycine or one of its derivatives selected from the group consisting of its salts, its phosphonate esters and its phosphonate ester salts.

31 Claims, No Drawings

(56) References Cited

FOREIGN PATENT DOCUMENTS

| | | |
|---|---|---|
| EP | 0537786 | 4/1993 |
| EP | 0595598 | 5/1994 |
| EP | 0638577 | 2/1995 |
| EP | 1681294 | 7/2006 |
| EP | 1681295 | 7/2006 |
| EP | 2112156 | 10/2009 |
| ES | 2018746 | 5/1991 |
| GB | 1142294 | 2/1969 |
| GB | 1230121 | 4/1971 |
| GB | 2154588 | 9/1985 |
| GB | 2154589 | 9/1985 |
| JP | 5775990 | 5/1982 |
| JP | 2007022956 | 2/2007 |
| RO | 101476 | 12/1991 |
| WO | 9415939 | 7/1994 |
| WO | 9422880 | 10/1994 |
| WO | 9640698 | 12/1996 |
| WO | 9819992 | 5/1998 |
| WO | 9835930 | 8/1998 |
| WO | 0002888 | 1/2000 |
| WO | 0009520 | 2/2000 |
| WO | 0014093 | 3/2000 |
| WO | 0192208 | 12/2001 |
| WO | 02055527 | 7/2002 |
| WO | 2006107824 | 10/2006 |
| WO | 2009068636 | 6/2009 |
| WO | 2009130322 | 10/2009 |
| WO | 2010055056 | 5/2010 |
| WO | 2010136574 | 12/2010 |
| WO | 2011039378 | 4/2011 |
| WO | 2011051309 | 5/2011 |

OTHER PUBLICATIONS

Tapia-Benavidis et al. Heterocycles 1997, vol. 45, p. 1679-1686, "Syntheses of N-Substituted 2,5-Piperazindiones."
International Search Report for PCT/EP2013/065125, Completed by the European Patent Office on Sep. 13, 2013, 3 Pages.
European Search Report for European Application No. 12176756, Completed by the European Patent Office on Jan. 9, 2013, 4 Pages.

METHOD FOR THE SYNTHESIS OF N-(PHOSPHONOMETHYL)GLYCINE

CROSS-REFERENCE TO RELATED APPLICATION

This application is the U.S. national phase of PCT Application No. PCT/EP2013/065125 filed on Jul. 17, 2013, which claims priority to EP Patent Application No. 12176756.0 filed on Jul. 17, 2012, the disclosures of which are incorporated in their entirety by reference herein.

FIELD OF THE INVENTION

The present invention is related to a novel method for the synthesis of N-(phosphonomethyl)glycine or its derivatives.

STATE OF THE ART

N-(phosphonomethyl)glycine, known in the agricultural chemical art as glyphosate, is a highly effective and commercially important broad spectrum phytotoxicant useful in controlling the growth of germinating seeds, emerging seedlings, maturing and established woody and herbaceous vegetation, and aquatic plants. Glyphosate is used as a systemic post-emergent herbicide to control the growth of a wide variety of annual and perennial grass and broadleaf weed species in cultivated crop lands, including cotton production.

Glyphosate and salts thereof are conveniently applied in aqueous herbicidal formulations, usually containing one or more surfactants, to the foliar tissues (i.e., the leaves or other photosynthesizing organs) of the target plant. After application, the glyphosate is absorbed by the foliar tissues and translocated throughout the plant. Glyphosate noncompetitively blocks an important biochemical pathway that is common to virtually all plants. More specifically, glyphosate inhibits the shikimic acid pathway that leads to the biosynthesis of aromatic amino acids. Glyphosate inhibits the conversion of phosphoenolpyruvic acid and 3-phosphoshikimic acid to 5-enolpyruvyl-3-phosphoshikimic acid by inhibiting the enzyme 5-enolpyruvyl-3-phosphoshikimic acid synthase (EPSP synthase or EPSPS) found in plants.

There are several well known manufacturing routes by which glyphosate can be prepared, for example the routes set out in U.S. Pat. No. 3,969,398; CA 1,039,739; U.S. Pat. No. 3,799,758; U.S. Pat. No. 3,927,080; U.S. Pat. No. 4,237,065 and U.S. Pat. No. 4,065,491 patents, but all of these routes present several drawbacks including product wastage, environmental problems and on top of that undesirable results from an economical point of view.

CH 620223 patent discloses a method for the preparation of N-(phosphonomethyl)glycine, in good yield, by hydrolysing bis-N,N'—[O,O'-[di-loweralkyl]-phosphonomethyl]-2,5-diketopiperazine (=compound I) with an aqueous hydrohalic acid. Compound I is prepared by reacting N,N'-bischloromethyl-2,5-diketopiperazine with a tri-loweralkylphosphite or by reacting the disodium salt of 2,5-diketopiperazine with chloromethylphosphonic acid.

ES 525399 patent discloses a method for the preparation of N-(phosphonomethyl)glycine, in good yield, by hydrolyzing, under alkali or acidic conditions, bis-N,N'[O,O' [dimethyl]-phosphonomethyl]-2,5-diketopiperazine (compound II). Compound II is prepared from reaction of 2,5-diketopiperazine with formaldehyde to form N,N'-dimethylol-2,5-diketopiperazine, which in a further reaction with thionyl chloride is converted into N,N'-bischloromethyl-2,5-diketopiperazine which in a subsequent step is converted into compound II through reaction with trimethylphosphite.

WO 98/35930 patent application discloses a method for the preparation of an N-acyl amino carboxylic acid which is readily converted to N-phosphonomethyl)glycine, or a salt or an ester thereof in a phosphonomethylation reaction. In one embodiment the phosphonomethylation reaction results in the replacement of the N-acyl substituent of the N-acyl amino carboxylic acid with an N-phosphonomethyl group. In another embodiment 2,5-diketopiperazine, formed by deacylation of N-acyl amino carboxylic acid, is phosphonomethylated with phosphorus trichloride, phosphorous acid or a source of phosphorous acid in the presence of a source of formaldehyde.

U.S. Pat. No. 4,804,499 patent discloses a process for the preparation of an N-substituted aminomethylphosphonic acid comprising reacting a 2,5-diketopiperazine compound with phosphorous acid and formaldehyde in an acidic medium. Example 4 illustrates the manufacture of N-(phosphonomethyl)glycine with a yield of 52%.

U.S. Pat. No. 4,400,330 patent discloses a method for the production of N-(phosphonomethyl)glycine which comprises the steps of: (1) first reacting 2,5-diketopiperazine with paraformaldehyde in glacial acetic acid, then adding a halogen substituted phosphorus compound, all in the presence of a low molecular weight carboxylic acid solvent, to form an intermediate N,N'-bisphosphonomethyl-2,5-diketopiperazine compound, (2) isolating said intermediate compound, (3) subsequently reacting said intermediate N,N'-bisphosphonomethyl-2,5-diketopiperazine compound with a hydrolyzing agent selected from an alkali or alkaline earth base to form a salt of N-(phosphonomethyl)glycine and, (4) thereafter acidifying said salt with a mineral acid to form the end product, N-(phosphonomethyl)glycine. Step (1) of U.S. Pat. No. 4,400,330 consists of the reaction of N,N'-dimethylol-2,5-diketopiperazine and a halogen substituted phosphorus compound resulting in the formation of N,N'-dihalomethyl-2,5-diketopiperazine and phosphorous acid. Phosphorous acid then reacts with N,N'-dihalomethyl-2,5-diketopiperazine to form N,N'-bisphosphonomethyl-2,5-diketopiperazine and hydrochloric acid.

Because of the importance of N-(phosphonomethyl)glycine as herbicide, other methods of making these compounds are constantly being sought.

AIMS OF THE INVENTION

The present invention aims to provide an improved, in particular an efficient and environmental-friendly method for the manufacture of N-(phosphonomethyl)glycine or its derivatives, which do not present the drawbacks of the methods of the state of the art.

SUMMARY OF THE INVENTION

The present invention discloses a method for the synthesis of N-(phosphonomethyl)glycine or one of its derivatives selected from the group consisting of its salts, its phosphonate esters and its phosphonate ester salts, comprising the steps of:

a) forming, in the presence of an acid catalyst, a reaction mixture comprising 2,5-diketopiperazine, formaldehyde and a compound comprising one or more P-O-P anhydride moieties, said moieties having one P atom at the oxidation state (+III) and the other P atom at the oxidation state (+IIII) or (+V), to form N,N'-bisphosphonomethyl-2,5-diketopiperazine, its mono- to tetra phosphonate esters, the dehydrated forms of N,N'-bisphosphonomethyl-2,5-diketopiperazine and the phosphonate esters of its dehydrated forms;

b) hydrolysing said N,N'-bisphosphonomethyl-2,5-diketopiperazine, its dehydrated forms or their phosphonate esters to obtain N-(phosphonomethyl)glycine or one of its derivatives selected from the group consisting of its salts, its phosphonate esters and its phosphonate ester salts.

Preferred embodiments of the present invention disclose one or more of the following features:

the molar ratio of formaldehyde to 2,5-diketopiperazine is comprised between 2 and 8, preferably between 2 and 3 and more preferably between 2.4 and 2.8;

the equivalent ratio of the N-H moiety of 2,5-diketopiperazine to the P-O-P anhydride moiety is comprised between 0.2 and 2.5, preferably between 0.3 and 2.0 and more preferably between 0.5 and 1.5;

the ratio of moles of acid catalyst to N—H equivalents of 2,5-diketopiperazine is 2 or more and is preferably comprised between 4 and 10;

the reactor content of step a) is stirred at a substantially constant temperature comprised between 20° C. and 120° C., preferably between 40° C. and 100° C. for a period of time comprised between 30 minutes and 24 hours and preferably between 1 hour and 20 hours;

the compound comprising the P-O-P anhydride moieties is selected from the group consisting of tetraphosphorus hexaoxide, tetraethylpyrophosphite and the compounds comprising P-O-P anhydride moieties obtained from the combination of one or more compounds comprising:

one or more P-OH moieties with one or more compounds comprising one or more P-O-P anhydride moieties or one or more P-X moieties, wherein the P atom of one or more compounds is at the oxidation state (+III);

one or more P-X moieties and water, wherein the P atom of the P-X moiety comprising compound is at the oxidation stage (+III);

two or more P-O-P moieties and water, wherein the P-O-P moiety comprising compound has a P atom at the oxidation state (+III) and a P atom at the oxidation state (+III) or (+V);

wherein the compounds having one or more P-OH moieties may be accessible by tautomerization of a >P(=O)H moiety, wherein X is a halogenide selected from the group consisting of chlorine, bromine and iodine and wherein the halogen level in the P-O-P anhydride moiety comprising compound is 1000 ppm or less, preferably 500 ppm or less and more preferably 200 ppm or less;

the compound comprising the P-O-P anhydride moieties is selected from the group consisting of tetraphosphorus hexaoxide, tetraethylpyrophosphite, and the P-O-P anhydride moiety comprising compound obtained from the combination of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water;

the compound comprising the P-O-P anhydride moieties is tetraphosphorus hexaoxide;

step a) is divided into two separate steps comprising:
 a1) reacting 2,5-diketopiperazine with formaldehyde to form N,N'-dimethylol-2,5 diketopiperazine;
 a2) reacting said N,N'-dimethylol-2,5-diketopiperazine with a compound comprising one or more P-O-P anhydride moieties, said moieties having one P atom at the oxidation state (+III) and the other P atom at the oxidation state (+III) or (+V), in the presence of an acid catalyst, to form N,N'-bisphosphonomethyl-2,5-diketopiperazine, its dehydrated forms or their derivatives;

the molar ratio of formaldehyde to 2,5-diketopiperazine is comprised between 2.0 and 8.0, preferably between 2.0 and 3.0 and more preferably between 2.4 and 2.8;

2,5-diketopiperazine is reacted with formaldehyde under aqueous alkali conditions at a pH above 7.0, preferably comprised between 7.1 and 11.0, more preferably between 7.5 and 10.0 and most preferably between 8.0 and 9.0;

step a1) of the reaction is obtained by heating at a temperature comprised between 60° C. and 100° C. and preferably between 70° C. and 90° C. for a period of time comprised between 20 minutes and 120 minutes;

N,N'-dimethylol-2,5 diketopiperazine, formed in step a1), is isolated;

step a2) comprises a solvent selected from the group consisting of 1,4-dioxane, toluene, ethylacetate, acetonitrile, acetic acid, sulfolane, 1-ethyl-3-methyl-imidazolium bis(trifluoromethylsulfonyl)imide, or a mixture thereof;

the P-O-P anhydride group comprising compound and N,N'-dimethylol-2,5-diketopiperazine, in the presence of an acid catalyst and optionally a solvent, are gradually mixed while maintaining the reaction temperature below 120° C.;

N,N'-dimethylol-2,5-diketopiperazine, as a solid or in solution, is gradually added to the P-O-P anhydride moiety comprising compound comprising an acid catalyst and optionally a solvent, while maintaining the reaction temperature below 120° C.;

the equivalent ratio of N,N'-dimethylol-2,5-diketopiperazine to the P-O-P anhydride moiety in step a2) is comprised between 0.2 and 2.5, preferably between 0.3 and 2.0 and more preferably between 0.5 and 1.5;

the molar ratio of N,N'-dimethylol-2,5-diketopiperazine to tetraphosphorus hexaoxide in step a2) is comprised between 0.5 and 5.0, preferably between 0.6 and 4.0 and more preferably between 1.0 and 3.0;

step a2), after completion of the addition of the P-O-P anhydride moiety comprising compound is optionally heated to a temperature comprised between 20° C. and 120° C., preferably between 40° C. and 100° C. and maintained at the said temperature for a period of time comprised between 1 hour and 20 hours;

N,N'-bisphosphonomethyl-2,5-diketopiperazine or its derivatives, formed in step a) or a2), are isolated;

the acid catalyst is a homogeneous Brønsted acid catalyst preferably selected from the group consisting of methanesulfonic acid, trifluoromethanesulfonic acid, trifluoroacetic acid, p-toluenesulfonic acid, hydrochloric acid, phosphorous acid, phosphoric acid and mixtures thereof;

the acid catalyst is a heterogeneous Brønsted acid preferably selected from the group consisting of:

(i) solid acidic metal oxide combinations as such or supported onto a carrier material;

(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;

(iii) organic sulfonic, carboxylic and phosphonic Brønsted acids which are substantially immiscible in the reaction medium at the reaction temperature;

(iv) an acid catalyst derived from:
 the interaction of a solid support having a lone pair of electrons onto which is deposited an organic Brønsted acid; or the interaction of a solid support having a lone pair of electrons onto which is deposited a compound having a Lewis acid site; or heterogeneous solids functionalized by chemical grafting with a Brønsted acid group or a precursor therefore; and (v) heterogeneous heteropolyacids of the general formula $H_xPM_yO_z$ wherein P is selected from phosphorus and silicon and M is selected from tungsten and molybdenum and combinations thereof;

the acid catalyst is a homogeneous Lewis acid preferably selected from the group consisting of $LiN(CF_3SO_2)_2$, $Mg(OCF_3SO_2)_2$, $Al(OCF_3SO_2)_3$, $Bi(OCF_3SO_2)_3$, $Sc(OCF_3SO_2)_3$;

the acid catalyst is a heterogeneous Lewis acid obtained from the interaction of a homogeneous Lewis acid catalyst and an organic or inorganic polymer compound;

the hydrolysis of step b) is performed under acid conditions, preferably obtained from a volatile acid preferably from hydrochloric acid;

the volatile acid is recovered at the end of step b) optionally purified and reused;

the hydrolysis of step b) is performed under alkali conditions;

the hydrolysis of step b) is performed under neutral conditions preferably in the presence of an enzymatic catalyst, preferably an amidase;

the hydrolysis of step b) occurs at a temperature comprised between 25° C. and 250° C. for a period of time comprised between 1 hour and 100 hours;

the derivatives are selected from the group consisting of N-(phosphonomethyl)glycine salts, phosphonate esters of N-(phosphonomethyl)glycine and phosphonate esters N-(phosphonomethyl)glycine salts and wherein the cation of the salt is selected from the group consisting of ammonium, isopropylammonium, ethanolammonium, dimethylammonium, trimethylsulfonium, sodium and potassium;

the N-(phosphonomethyl)glycine is obtained in a batch, or a continuous process;

The formula for the reactions set forth above, can be represented as follows:

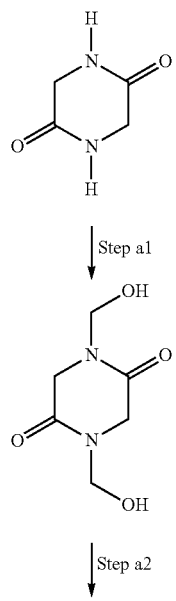

-continued

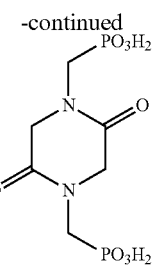

Step b

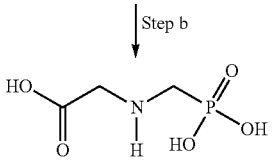

The above intermediate reactions are presumed to be one of the multiple possibilities for obtaining N-(phosphonomethyl)glycine or its derivatives.

DETAILED DESCRIPTION OF THE INVENTION

The present invention provides an efficient, economical and preferably environmental friendly method for the manufacture of N-(phosphonomethyl)glycine or its derivatives.

Under derivatives the present invention understands salts and phosphonate esters of N-(phosphonomethyl)glycine wherein:

the N-(phosphonomethyl)glycine salts comprise the carboxylate and/or (di) phosphonate anion and an agronomically acceptable cation or the ammonium cation of N-(phosphonomethyl)glycine and an agronomically acceptable anion. Preferred salts are the ammonium, the isopropylammonium, the ethanolammonium, the dimethylammonium, the trimethylsulfonium, the sodium and the potassium salts wherein the ratio of the cation to the N-(phosphonomethyl)glycine anion is comprised between 0.1 and 3.0.

When hydrolysis is performed under base conditions, the salt comprises the carboxylate and/or phosphonate anion of N-(phosphonomethyl)glycine and an alkali metal, alkaline earth metal or ammonium cation; otherwise, when hydrolysis is performed under acid conditions, the formed salt comprises the ammonium cation of N-(phosphonomethyl)glycine and the anion coming from the acid used for the hydrolysis. In this particular last case, the anion is for example the chloride anion, coming from hydrochloric acid, or the sulfate anion coming from sulfuric acid.

the phosphonate esters comprise one or more substituted or unsubstituted hydrocarbyl groups which may be branched or unbranched, saturated or unsaturated and may contain one or more rings. Suitable hydrocarbyls include alkyl, alkenyl, alkynyl and aryl moieties. They also include alkyl, alkenyl, alkynyl and aryl moieties substituted with other aliphatic or cyclic hydrocarbyl groups, such as alkaryl, alkenaryl and alkynaryl.

The substituted hydrocarbyl is defined as a hydrocarbyl wherein at least one hydrogen atom has been substituted with an atom other than hydrogen such as an halogen atom, an oxygen atom to form for example an ether or an ester, a nitrogen atom to form an amide or nitrile group or a sulfur atom to form for example a thioether group.

The method of the present invention includes the steps of:

a) reacting 2,5-diketopiperazine, formaldehyde and a compound comprising one or more P-O-P anhydride moieties, said moieties having one P atom at the oxidation state (+III) and the other P atom at the oxidation state (+III) or (+V), in the presence of an acid catalyst and optionally a solvent, to form N,N'-bisphosphonomethyl-2,5-diketopiperazine, its dehydrated forms or derivatives thereof;

b) hydrolysing the formed N,N'-bisphosphonomethyl-2, 5-diketopiperazine, its dehydrated forms or their derivatives to form N-(phosphonomethyl)glycine or one of its derivatives.

Under derivatives of N,N'-bisphosphonomethyl-2,5-diketopiperazine and its dehydrated forms, the present invention understands mono- to tetra phosphonate esters of N,N'-bisphosphonomethyl-2,5-diketopiperazine or the phosphonate esters of its dehydrated forms. Phosphonate esters in general are prepared by using the compound comprising one or more P-O-P anhydride moieties substituted with the corresponding hydrocarbyl substituents.

The derivatives of N-(phosphonomethyl)glycine preferably are obtained as such as an outcome of the hydrolysis of reaction step b) or can be obtained by further treatment of N-phosphonomethylglycine. Under derivatives the present invention understands salts, phosphonate esters, or phosphonate ester salts of N-(phosphonomethyl)glycine. In the present invention it is understood that the expression N-(phosphonomethyl)glycine comprises all derivatives.

The molar ratio of formaldehyde to 2,5-diketopiperazine is comprised between about 2 and about 8, preferably between about 2 and about 3 and more preferably between about 2.4 and about 2.8.

The equivalent ratio of the N-H moiety of 2,5-diketopiperazine to the P-O-P anhydride moiety is comprised between about 0.2 and about 2.5, preferably between about 0.3 and about 2.0 and more preferably between about 0.5 and about 1.5.

The ratio of moles of acid catalyst to N—H equivalents of 2,5-diketopiperazine is at least about 2 and is preferably comprised between about 4 and about 10.

The reactor content of step a) is stirred at a substantially constant temperature comprised between about 20° C. and about 120° C., preferably between about 40° C. and about 100° C. for a period of time comprised between about 30 minutes and about 24 hours and preferably between about 1 hour and about 20 hours.

2,5-diketopiperazine may be obtained from the cyclodimerization of glycine as disclosed in for example US patent application 2004/0024180 wherein glycine is heated, in an organic solvent, at a temperature between about 50° C. and about 200° C., in particular at a temperature comprised between about 80° C. and about 150° C. The pH range wherein cyclodimerisation takes place is advantageously between about 2 to about 9 and preferably between about 3 to about 7.

In general, solvents that can be used for the cyclodimerization reaction of glycine are preferably those capable of forming a low-boiling azeotrope with water. Such solvents are for example acetonitrile, allyl alcohol, benzene, benzyl alcohol, n-butanol, 2-butanol, tert.-butanol, acetic acid butylester, carbon tetrachloride, chlorobenzene, chloroform, cyclohexane, 1,2-dichlorethane, diethylacetal, dimethylacetal, acetic acid ethylester, heptane, methylisobutylketone, 3-pentanol, toluene and xylene.

Formaldehyde known as oxymethylene having the formula $CH_2O$ is produced and sold as water solutions containing variable, frequently minor, e.g. 0.3-3%, amounts of methanol and are typically reported on a 37% formaldehyde basis although different concentrations can be used. Formaldehyde solutions exist as a mixture of oligomers. Such formaldehyde precursors can, for example, be represented by paraformaldehyde, a solid mixture of linear poly(oxymethylene glycols) of usually fairly short, n=8-100, chain length, and the cyclic trimer of formaldehyde designated by the terms 1,3,5-trioxane. Concentrations of liquid formaldehyde above about 37% need to be kept above room temperature to prevent the precipitation of formaldehyde polymers. The temperature necessary to maintain a clear solution and prevent separation of solid polymer increases from room temperature as the solution concentration is increased above about 37%.

While formaldehyde is generally used as 37% by weight solution in water, known as formalin, it also can be added as an aqueous solution with a formaldehyde concentration different from 37% by weight or as a solid such a for example as paraformaldehyde or as 1,3,5-trioxane.

For the case wherein 2,5-diketopiperazine, formaldehyde and the P-O-P anhydride moiety comprising compound, having one P atom at the oxidation state (+III) and the other P atom at the oxidation state (+III) or (+V), are forming a reaction mixture, it goes without saying that the water quantity, present in the aqueous solution of formaldehyde is in accordance with the one required for transforming a first P-O-P anhydride moiety comprising compound into a modified P-O-P-anhydride moiety comprising compound through partially hydrolysis of said first P-O-P anhydride moiety comprising compound whereupon said modified P-O-P anhydride moiety comprising compound will react to form N,N'-bisphosphonomethyl-2,5-diketopiperazine, its dehydrated forms or derivatives thereof. For this particular case, formaldehyde preferably is added under anhydrous conditions, i.e. formaldehyde preferably is added as an anhydrous solid.

While the P-O-P anhydride moiety comprising compound preferably is selected from the group consisting of tetraphosphorus hexaoxide and partially hydrolysed species of tetraphosphorus hexaoxide obtained through reaction of 1 mole of tetraphosphorus hexaoxide with 1, 2, 3, 4 and 5 moles of water respectively, it is understood that all compounds comprising at least one P-O-P anhydride moiety wherein one P atom is at the oxidation state (+III) and the other P atom is at the oxidation state (+III) or (+V) can be used for the purpose of the invention.

Suitable P-O-P anhydride moiety comprising compounds can either comprise a P-O-P anhydride moiety in the compound itself (e.g. $P_4O_6$ or pyrophosphites $(RO)_2P-O-P(OR)_2$) or be generated in situ by combining reagents that will form the required P-O-P anhydride moiety.

Suitable reagent combinations are:

a) compounds containing a least one P-OH moiety (also accessible by tautomerisation of a >P(=O)H moiety into >P(LP)OH (where LP stands for lone pair of electrons)) such as for example is the case for dimethylphosphite $(MeO)_2P(=O)H$ and compounds containing at least one P-O-P anhydride moiety e.g. $P_2O_5$ or $P_4O_6$;

b) compounds containing at least one P-OH moiety and compounds containing at least one P-X (X=Cl, Br, I) moiety;

c) compounds containing at least one P-X moiety and $H_2O$;

d) compounds containing P-O-P anhydride moieties and $H_2O$ for partial hydrolysis.

In case a) and b) it is mandatory that at least in one of the utilised compounds the P atom is in the oxidation state (+III) whereas in case c) the P atom has to be in the oxidation state (+III) and in case d) the P-O-P moieties have one P atom at the oxidation state (+III) and the other P atom at the oxidation state (+III) or (+V), in order to form the P-O-P anhydride moiety comprising compound, having one P atom at the oxidation state (+III) and the other P atom at the oxidation state (+III) or (+V).

P-O-P anhydride moiety comprising compounds wherein the P-O-P anhydride moiety is already present are phosphorus oxides with the formula $P_4O_n$ with n=6-9, pyrophosphites with the general formula $(RO)_2P$-O-$P(OR)_2$ wherein R is an alkyl or aryl group, pyrophosphorous acid ($H_4P_2O_5$) and isohypophosphoric acid (H)(HO)P(O)—O—P(O)(OH)$_2$.

Combinations described under a) are obtained by reacting e.g. phosphorus oxides with formula $P_4O_n$ with n=6-10, alkyl substituted pyrophosphites, pyrophosphorous acid, isohypophosphoric acid, metaphosphoric acid or polyphosphoric acid with phosphorous acid, phosphoric acid, mono or disubstituted phosphites with formula $(RO)PO_2H_2$ or $(RO)_2POH$ wherein R is an alkyl or aryl group, phosphate esters $(RO)PO_3H_2$ or $(RO)_2PO_2H$, phosphonic acids $RPO_3H_2$ or its monoester $RPO_2H(OR)$ with the proviso that such combinations will lead to P-O-P anhydride moiety comprising compounds having one P atom at the oxidation state (+III) and the other P atom at the oxidation state (+III) or (+V).

Combinations described under b) are obtained by combining $PCl_3$, $PBr_3$, $POCl_3$, or mono or dichloro phosphites like $(RO)_2PCl$ and $(RO)PCl_2$ with phosphorous acid, phosphoric acid, or mono or disubstituted phosphites with formula $(RO)PO_2H_2$ or $(RO)_2POH$ with the proviso that such combinations will lead to P-O-P anhydride moiety comprising compound having one P atom at the oxidation state (+III) and the other P atom at the oxidation state (+III) or (+V).

Combinations described under c) are obtained by combining $PCl_3$, $PBr_3$, or mono or dichloro phosphites like $(RO)_2PCl$ and $(RO)PCl_2$ with $H_2O$.

In order to obtain a P-O-P anhydride moiety comprising compounds free of P-X functions the remaining P-X functions are hydrolysed with water. Remaining P-O-P anhydride moieties can also be hydrolysed as long as the required P-O-P anhydride moiety wherein one P atom is at the oxidation state (+III) and the other P atom is at the oxidation state (+III) or (+V) remains.

Most preferred are tetraphosphorus hexaoxide, tetraethylpyrophosphite and the combinations of phosphorous acid and tetraphosphorus hexaoxide, of phosphorous acid and tetraphosphorus decaoxide, of phosphorous acid and phosphorus trichloride, of dimethyl phosphite and tetraphosphorus decaoxide, of phosphorus trichloride and water and of tetraphosphorus hexaoxide and water.

The amount of 'reactive' P(+III) atoms that can be converted into phosphonic acids, according to this invention, is determined by the amount of P(+III) atoms and the amount of P-O-P anhydride moieties. If there are more P-O-P anhydride moieties than P(+III) atoms then all P(+III) atoms are converted into phosphonic acids. If there are less P-O-P anhydride moieties than P(+III) atoms then only a part of P(+III) atoms equal to the amount of P-O-P anhydride moieties is converted into phosphonic acids.

In the event, halogen containing starting materials, e.g. $PCl_3$, $POCl_3$ or $PBr_3$ are used, the level of halogen in the P-O-P anhydride comprising compound shall be kept below 1000 ppm, usually below 500 ppm, preferably below 200 ppm, expressed in relation to the P-O-P material being 100%. Therefore, all excess P-X functions are hydrolysed before the reactions with the substrate by addition of one molecule of $H_2O$ per excess P-X function. The formed HX is removed by e.g. blowing a dry inert gas, like nitrogen or helium, through the solution.

The tetraphosphorus hexaoxide preferably used within the scope of the present invention may be represented by a substantially pure compound containing at least 85%, preferably more than 90%, more preferably at least 95% and in one particular execution at least 97% of $P_4O_6$. While tetraphosphorus hexaoxide, suitable for use within the context of this invention, may be manufactured by any known technology, in preferred executions it is prepared in accordance with the method described in WO 2009/068636 and/or WO 2010/055056 patent applications under the section entitled "Process for the manufacture of $P_4O_6$ with improved yield". In detail, oxygen, or a mixture of oxygen and inert gas, and gaseous or liquid phosphorus are reacted in essentially stoichiometric amounts in a reaction unit at a temperature in the range from 1600 to 2000 K, by removing the heat created by the exothermic reaction of phosphorus and oxygen, while maintaining a preferred residence time of from 0.5 to 60 seconds followed by quenching the reaction product at a temperature below 700 K and refining the crude reaction product by distillation. Tetraphosphorus hexaoxide so prepared is a pure product containing usually at least 97% of the oxide. The so produced $P_4O_6$ is generally represented by a liquid material of high purity containing in particular low levels of elementary phosphorus, $P_4$, preferably below 1000 ppm, expressed in relation to the $P_4O_6$ being 100%. The preferred residence time is from 5 to 30 seconds, more preferably from 8 to 30 seconds. The reaction product can, in one preferred execution, be quenched to a temperature below 350 K.

It is presumed that the $P_4O_6$ participating in a reaction at a temperature of from 24° C. (melting t°) to 120° C. is necessarily liquid or gaseous although solid species can, academically speaking, be used in the preparation of the reaction medium.

For reasons of convenience and operational expertise, the tetraphosphorus hexaoxide, represented by $P_4O_6$, is of high purity and contains very low levels of impurities, in particular elemental phosphorus, $P_4$, at a level below 1000 ppm, usually below 500 ppm and preferably not more than 200 ppm, expressed in relation to the $P_4O_6$ being 100%.

The acid catalyst used within the scope of the present invention is preferably a homogeneous Brønsted acid catalyst, optionally in the presence of a solvent, or a heterogeneous Brønsted acid catalyst, in the presence of a solvent, or a Lewis acid catalyst, in the presence of a solvent.

The homogeneous Brønsted acid preferably is selected from the group consisting of methanesulfonic acid, fluoromethanesulfonic acid, trichloromethanesulfonic acid, trifluoromethanesulfonic acid, trifluoroacetic acid, tert-butylsulfonic acid, p-toluenesulfonic acid, naphthalene sulfonic acid, 2,4,6-trimethylbenzene-sulfonic acid, perfluoro or perchloro alkyl sulfonic acids, perfluoro or perchloro alkyl carboxylic acids, hydrochloric acid, hydrobromic acid, hydroiodic acid, phosphorous acid, phosphoric acid, and mixtures thereof. The homogeneous Brønsted acid is preferably methanesulfonic acid.

The heterogeneous Brønsted acid is preferably selected from the group consisting of:
(i) solid acidic metal oxide combinations as such or supported onto a carrier material;
(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;

(iii) organic sulfonic, carboxylic and phosphonic Brønsted acids which are substantially immiscible in the reaction medium at the reaction temperature;

(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid group or a precursor therefore; and (v) heterogeneous heteropolyacids of the general formula $H_xPM_yO_z$ wherein P is selected from phosphorus and silicon and M is selected from tungsten and molybdenum and combinations thereof.

Preferred homogeneous Lewis acids can be selected from metal salts having the general formula:

$$MX_n$$

wherein M represents a main group element or transition metal like Li, B, Mg, Al, Bi, Fe, Zn, La, Sc, Yb, or Pd; X in $MX_n$ is typically an anion of an acid or acid derivative like Cl, OTf or $NTf_2$, where Tf stands for $CF_3SO_2$ and n is equal to the oxidation state of M, which can be from 1 to 5. Possible combinations are e.g. $LiNTf_2$, $Mg(OTf)_2$, $MgCl_2$, $ZnCl_2$, $PdCl_2$, $Fe(OTf)_3$, $Al(OTf)_3$, $AlCl_3$, $Bi(OTf)_3$, $BiCl_3$, $Sc(OTf)_3$, $Ln(OTf)_3$, $Yb(OTf)_3$. Preferably, combinations of a hard metal or a metal on the borderline between hard and soft according to the HSAB (hard soft acid base) concept like Li, Mg, Al, Sc, Zn, Bi, and weakly coordinating anions like OTf or $NTf_2$ are used. Examples of such preferred combinations are $LiNTf_2$, $Mg(OTf)_2$, $Al(OTf)_3$, $Bi(OTf)_3$.

Preferred heterogeneous Lewis acids can be represented by species of discretionary selected subclasses created by interaction/bonding of homogeneous Lewis acids e.g. metal complexes, metal salts or organometallic species with polymeric organic or inorganic backbones. An example of such subclass is a polystyrene matrix with bonded $Sc(OTf)_2$ groups. Such catalyst can be prepared e.g. by interaction of a polystyrene sulfonic acid resin, e.g. Amberlyst 15, with $Sc(OTf)_3$. The number of equivalents of Lewis acid functions can be determined in this case by different ways e.g. by acid base determination of the unreacted sulfonic acid groups, by quantitative determination of the liberated triflic acid and by ICP measurement of the amount of Sc on the resin.

In the method of the present invention solvents are optionally used. Typical examples of suitable solvents are anisole; acetic acid; chlorinated and fluorinated hydrocarbons such as fluorobenzene, chlorobenzene, tetrachloroethane, tetrachloroethylene, dichloroethane, dichloromethane; polar solvents like diglyme, glyme, diphenyloxide, polyalkylene glycol derivatives with capped OH groups such as OR* where R* is a low alkyl or acyl group; aliphatic hydrocarbons such as hexane, heptane, cyclohexane; non-cyclic ethers like dibutyl ether, diethyl ether, diisopropyl ether, dipentylether, and butylmethylether; cyclic ethers like tetrahydrofuran, dioxane, and tetrahydropyran; mixed cyclic/non-cyclic ethers like cyclopentylmethylether; cyclic and non-cyclic sulfones like sulfolane; aromatic solvents like toluene, benzene, xylene; organic acetates like ethylacetate; organic nitriles like acetonitrile, benzonitrile; silicon fluids like polymethylphenyl siloxane or mixtures thereof;

non reactive ionic liquids like 1-n-butyl-imidazolium trifluoromethanesulfonate, and 1-ethyl-3-methyl-imidazolium bis(trifluoromethylsulfonyl)imide; or a mixture thereof.

In a particular embodiment of the present invention the acid catalyst acts as catalyst and as solvent.

In a preferred embodiment of the present invention the method comprises the steps of:

a1) reacting 2,5-diketopiperazine with formaldehyde, to form N,N'-dimethylol 2,5-diketopiperazine;

a2) reacting N,N'-dimethylol-2,5-diketopiperazine with a compound comprising one or more P-O-P anhydride moieties, said moieties having one P atom at the oxidation state (+III) and the other P atom at the oxidation state (+III) or (+V), in the presence of an acid catalyst and optionally a solvent, to form N,N'-bisphosphonomethyl-2,5-diketopiperazine or its dehydrated forms or derivatives thereof, dependent on the P-O-P anhydride moiety comprising compound used for reacting with the N,N'-dimethylol 2,5-diketopiperazine;

b) hydrolysing the formed N,N'-bisphosphonomethyl-2,5-diketopiperazine or its dehydrated forms or their derivatives to form N-(phosphonomethyl)glycine or one of its derivatives.

In step a1) 2,5-diketopiperazine is reacted with formaldehyde, preferably under aqueous alkali conditions obtained by dissolving a base, wherein the base is preferably selected from the group consisting of sodium carbonate, potassium carbonate, calcium carbonate, sodium bicarbonate, potassium bicarbonate, sodium acetate, potassium acetate, sodium hydroxide, potassium hydroxide, or a mixture thereof.

In step a1), the molar ratio of formaldehyde to 2,5-diketopiperazine is comprised between about 2 and about 8, preferably between about 2 and about 3 and more preferably between about 2.4 and about 2.8.

The process of the present invention is started by making a suspension of 2,5-diketopiperazine in water and adjusting the pH to a value above about 7, preferably comprised between about 7.1 and about 11.0, more preferably between about 7.5 and about 10.0 and most preferably between about 8.0 and about 9.0 through the addition of an aqueous solution of a base, wherein the resulting suspension comprises between about 5% and about 50% by weight, preferably between about 10% and about 40% by weight and more preferably between about 15% and about 35% by weight of 2,5-diketopiperazine.

Formaldehyde, preferably an aqueous solution of formaldehyde, is added to the aqueous suspension comprising 2,5-diketopiperazine under stirring. Preferably addition of formaldehyde to the aqueous solution of 2,5-diketopiperazine is performed at room temperature i.e. between about 15° C. and about 30° C., whereupon the resulting suspension is heated up to a temperature comprised between about 60° C. and about 100° C.

Advantageously, the reaction of 2,5-diketopiperazine with formaldehyde is performed under stirring at a temperature comprised between about 60° C. and about 100° C., preferably between about 70° C. and about 90° C., more preferably at about 85° C. for a period of time comprised between about 20 minutes and about 120 minutes preferably about 60 minutes.

After completion of the reaction of 2,5-diketopiperazine with formaldehyde, the formed N,N'-dimethylol-2,5-diketopiperazine is isolated through precipitation and filtration. Therefore the reactor content is cooled down to a temperature below about 60° C., preferably to a temperature comprised between about 10° C. and about 40° C. and more preferably between about 15° C. and about 30° C. whereupon precipitation of N,N'-dimethylol-2,5-diketopiperazine starts. Further cooling to a temperature comprised between about 2° C. and about 10° C. for a period of time comprised between about 4 hours and about 20 hours completes the precipitation process.

The precipitate of N,N'-dimethylol-2,5-diketopiperazine is isolated using conventional filtration techniques. The precipitate of N,N'-dimethylol-2,5-diketopiperazine is washed with cold water and optionally a polar solvent such as ethanol and finally dried by air or by forced drying techniques, such as for example convection.

In the preferred embodiment of the present invention the filtrate, also called the mother liquor, is advantageously reused in a subsequent preparation of N,N'-dimethylol-2,5-diketopiperazine, substituting the water, used for preparing the suspension. For this case the formalin quantity to be introduced in step a1) can be reduced, taking into account the formaldehyde content of the mother liquor.

The yield of the conversion of 2,5-diketopiperazine into N,N'-dimethylol-2,5-diketopiperazine is preferably at least about 85%.

In step a2) N,N'-dimethylol-2,5-diketopiperazine is suspended in the acid catalyst or in a solvent comprising the acid catalyst, wherein the resulting suspension comprises between about 2.5% and about 25% by weight and preferably between about 5% and about 20% by weight of N,N'-dimethylol 2,5-diketopiperazine.

The suspension is preferably heated to a temperature comprised between about 40° C. and about 80° C., more preferably between about 50° C. and about 70° C. under stirring, or kept below about 40° C. and using ultrasounds, in order to convert the suspension into a solution. The solvent is required for the specific case where the homogeneous acid catalyst does not solubilize N,N'-dimethylol 2,5-diketopiperazine.

Once N,N'-dimethylol-2,5-diketopiperazine dissolved in the acid catalyst or in the solvent comprising the acid catalyst, the P-O-P anhydride moiety comprising compound, preferably tetraphosphorus hexaoxide, and the solution comprising N,N'-dimethylol 2,5-diketopiperazine, standing at a temperature comprised between about 0° C. and about 60° C., are gradually mixed, under stirring, in such a way that, during the mixing, the temperature of the reaction mixture does not exceed about 120° C., preferably about 90° C. and more preferably about 60° C.

In step a2) the ratio of moles of acid catalyst to equivalents of P-O-P anhydride moiety, having one P atom at the oxidation state (+III) and the other P atom at the oxidation state (+III) or (+V), is at least about 1 and is preferably comprised between about 2 and about 10.

In step a2) the ratio of moles of acid catalyst to hydroxyl equivalents of N,N'-dimethylol-2,5-diketopiperazine is at least about 2 and is preferably comprised between about 4 and about 10.

The equivalent ratio of N,N'-dimethylol-2,5-diketopiperazine to the P-O-P anhydride moiety in step a2) is comprised between about 0.2 and about 2.5, preferably between about 0.3 and about 2.0 and more preferably between about 0.5 and about 1.5.

The P-O-P anhydride moiety comprising compound is preferably tetraphosphorus hexaoxide. The molar ratio of N,N'-dimethylol-2,5-diketopiperazine to tetraphosphorus hexaoxide in step a2) is comprised between about 0.4 and about 5.0, preferably between about 0.6 and about 4.0 and more preferably between about 1.0 and about 3.0.

The gradual mixing of the P-O-P anhydride moiety comprising compound, preferably tetraphosphorus hexaoxide, and the solution comprising N,N'-dimethylol-2,5-diketopiperazine is performed under optimal mixing conditions. Once the addition of the P-O-P anhydride moiety comprising compound, preferably tetraphosphorus hexaoxide, is completed, the reactor content is stirred at a substantially constant temperature comprised between about 20° C. and about 120° C., preferably between about 40° C. and about 100° C. for a period of time comprised between about 1 hour and about 20 hours and preferably between about 4 hours and about 16 hours.

In the preferred embodiment of the present invention N,N'-dimethylol 2,5-diketopiperazine, as a solid or solubilized in the acid catalyst and/or in a solvent, preferably is gradually added, under optimal mixing conditions, to a mixture comprising the P-O-P anhydride moiety comprising compound, optionally the acid catalyst and optionally a solvent.

In another embodiment of the present invention step a1) and step a2) are performed successively i.e. step a2) is initiated and completed without the isolation of N,N'-dimethylol-2,5-diketopiperazine at the end of step a1). For this particular embodiment, step a1) is performed under acid conditions preferably obtained from methanesulfonic acid whereby the formaldehyde is preferably added as an anhydrous solid.

In a preferred embodiment of the present invention, N,N'-bisphosphonomethyl-2,5-diketopiperazine or its dehydrated forms or a derivative thereof is isolated after completion of step a) or a2). Therefore the reactor content of step a) or a2) is quenched through the addition of water; the amount of added water is comprised between about 1 and about 40 equivalents per mole of the starting 2,5-diketopiperazine or N,N'-dimethylol-2,5-diketopiperazine. Preferably the amount of added water is comprised between about 6 to about 30 equivalents per mole of the starting 2,5-diketopiperazine or N,N'-dimethylol-2,5-diketopiperazine.

The precipitate of N,N'-bisphosphonomethyl-2,5-diketopiperazine or the derivatives thereof, formed upon quenching is isolated using conventional filtration techniques, washed with cold water and optionally dried by air drying or by using forced drying techniques, such as for example convection.

The yield of the conversion of N,N'-dimethylol-2,5-diketopiperazine into N,N'-bisphosphonomethyl-2,5-diketopiperazine or a derivative thereof, obtained according to the method of the present invention, is preferably at least about 75%.

The aqueous acid catalyst solution, preferably the aqueous methanesulfonic acid solution, obtained as the filtrate after the isolation of N,N'-bisphosphonomethyl-2,5-diketopiperazine or one of its derivatives contains between about 5% and about 35% water by weight. For reusing the acid catalyst in another cycle of step a) or a2) it can be purified by techniques known in the art, like e.g. thin film or falling film evaporation, to remove the excess water.

After completion of step a) or a2), the reactor content of step a) or a2) is hydrolysed in step b) and the glyphosate is isolated as a free base or a salt using known procedures from the literature.

During the hydrolysis, N,N'-bisphosphonomethyl-2,5-diketopiperazine or one of its derivatives is converted into N-(phosphonomethyl) glycine.

Hydrolysis is performed under acidic, neutral or alkali conditions in a batch or continuous process.

When the hydrolysis is performed under neutral conditions the addition of an enzymatic catalyst is optional. The enzymatic hydrolysis is preferably carried out in the presence of an amidase.

When the hydrolysis is performed under acid or alkali conditions, the molar ratio of acid or base to N,N'-bisphosphonomethyl-2,5-diketopiperazine or one of its derivatives is comprised between about 1 and about 20 and preferably between about 2 and about 15.

The alkali aqueous solution used for the hydrolysis of N,N'-bisphosphonomethyl-2,5-diketopiperazine or one of its derivatives is preferably obtained from a base selected from the group consisting of alkali hydroxides, alkaline earth hydroxides, ammonia and primary aliphatic amines; preferably said base is sodium hydroxide or potassium hydroxide The acid aqueous solution used for the hydrolysis of N,N'-bisphosphonomethyl-2,5-diketopiperazine or one of its derivatives is preferably obtained from a mineral acid; preferably said mineral acid is volatile and most preferable this acid is hydrochloric acid.

Preferably the hydrolysis is performed under acid conditions; more preferably the acid conditions are obtained from an aqueous solution of hydrochloric acid.

The hydrolysis is performed in step b) through the addition of an acid, neutral or alkali aqueous solution to the N,N'-bisphosphonomethyl-2,5-diketopiperazine or its derivatives of step a) or a2) after completion of step a) or a2).

N,N'-bisphosphonomethyl-2,5-diketopiperazine or a derivative thereof is suspended in an acid, neutral or alkali aqueous solution, wherein the resulting suspension comprises between about 10% and about 50% by weight and preferably between about 20% and about 40% by weight of N,N'-bisphosphonomethyl-2,5-diketopiperazine or one of its derivatives.

The hydrolysis of step b), under acid or alkali conditions, is performed at a temperature comprised between about 90° C. and about 230° C. and preferably between about 110° C. and about 190° C., in a sealed reactor under autogenous pressure, for a period of time comprised between about 1 hour and about 50 hours and preferably between about 5 hours and about 40 hours.

The hydrolysis of step b), under neutral conditions is advantageously performed at a temperature comprised between about 180° C. and about 250° C. for a period of time comprised between about 4 hours and about 80 hours.

The hydrolysis of step b), under neutral conditions in the presence of an enzymatic catalyst, preferably an amidase, is advantageously performed at a temperature comprised between about 25° C. and about 80° C. for a period of time comprised between about 2 hours and about 100 hours.

The yield of the conversion of N,N'-bisphosphonomethyl-2,5-diketopiperazine or one of its derivatives into N-(phosphonomethyl)glycine or one of its derivatives, according to the method of the present invention, is advantageously at least about 95%.

For step b) being performed under acid conditions, in particular when volatile acids are used such as for example hydrochloric acid, the acid may be recovered at the end of step b), optionally purified and reused. The excess of HCl may be removed by distillation under atmospheric or reduced pressure. Further, the removal of the volatile acid implies that N-phosphonomethylglycine, as such, can be obtained.

For step b) being performed under basic conditions when volatile basic reagents are used such as for example ammonia, the base may be recovered at the end of step b), optionally purified and reused. The excess ammonia may be removed by distillation under atmospheric or reduced pressure.

On the other hand, performing step b) in the presence of non volatile acids or bases results in the formation of N-(phosphonomethyl)glycine salts, which further can be treated with respectively a base or an acid in order to convert said N-(phosphonomethyl)glycine salts into N-(phosphonomethyl)glycine.

In a particular embodiment of the present invention step a) and step b) or step a2) and step b) are performed successively i.e. step b) is initiated and completed without the isolation of N,N'-bisphosphonomethyl-2,5-diketopiperazine or the derivatives thereof at the end of step a) or step a2). Both, step a) or step a2) and step b) preferably are performed under acid conditions.

In another embodiment of the present invention step a1), step a2) and step b) are performed successively i.e. step b) is initiated and completed without the isolation of N,N'-bisphosphonomethyl-2,5-diketopiperazine or its derivatives at the end of step a2), while step a2) is initiated and completed without the isolation of N,N'-dimethylol-2,5-diketopiperazine at the end of step a1). All steps a1), a2) and b) preferably are performed under acid conditions. Preferably methanesulfonic acid and/or hydrochloric acid are used.

For the particular case that step a) and step b) or step a1), step a2) and step b) are performed successively, step a) or step a1) and step a2) must be performed under anhydrous conditions while step b) is performed under aqueous conditions.

EXAMPLES

The following examples illustrate the invention; they are merely meant to exemplify the present invention but are not destined to limit or otherwise define the scope of the present invention.

Example 1 to Example 3 illustrate step a1) of the present invention i.e. the reaction of 2,5-diketopiperazine and formaldehyde to form N,N'-dimethylol-2,5-diketopiperazine.

Example 4 to Example 21 illustrate step a2) of the present invention i.e. the reaction of N,N'-dimethylol-2,5-diketopiperazine with a P-O-P anhydride moiety comprising compound having one P atom at the oxidation state (+III) and the other P atom at the oxidation state (+III) or (+V), in the presence of an acid catalyst, to form N,N'-bisphosphonomethyl-2,5-diketopiperazine. For Example 4 to Example 17, the P-O-P anhydride moiety comprising compound is tetraphosphorus hexaoxide.

Example 22 illustrates step a1) and step a2) successively performed without the isolation of the product of step a) (N,N'-dimethylol-2,5-diketopiperazine).

Example 23 to 37 illustrate step b) i.e. the hydrolysis.

Example 38 illustrates step a2) and step b) successively performed without the isolation of the product of step a2) (N,N'-bisphosphonomethyl-2,5-diketopiperazine).

Example 39 illustrates step a1), step a2) and step b) successively performed without the isolation of the product of step a1) (N,N'-dimethylol-2,5-diketopiperazine) and without the isolation of the product of step a2) (N,N'-bisphosphonomethyl-2,5-diketopiperazine).

Example 40 illustrates step a) wherein tetraphosphorus hexaoxide is added to a mixture of 2,5-diketopiperazine and 1,3,5-trioxane in the presence of methanesulfonic acid at 40° C.

Example 41 and 42 illustrate the glyphosate salt formulation after completion of step b).

Example 1 (Step a)

In a round bottom flask equipped with a stirrer, a water cooled condenser and a thermocouple attached to a thermoregulator, 11.41 g (0.1 mole) 2,5-diketopiperazine was suspended in 40 ml of water by stirring. The pH was adjusted to a value of about 8 through the addition of a few drops of a 50% w/w aqueous solution of potassium carbonate. Thereupon 20.5 ml of 37% w/w formalin were added, while stirring, and the resulting suspension was heated to a temperature of 85° C. and maintained at that temperature for 1 hour.

The suspension was then cooled down to room temperature whereupon a white solid starts to precipitate. After 10 hours at 4° C., the precipitation was completed and the precipitate was filtered with the aid of a Buchner funnel. The filtrate, also called the mother liquor was recovered and reused in synthesis of example 2.

The precipitate subsequently was washed with cold water and ethanol and finally dried to yield 15.12 g (0.087 mole) N,N'-dimethylol-2,5-diketopiperazine (yield=87%) with a purity of 98%.

Example 2 (Step a1)

Using the equipment of Example 1, 11.41 g (0.1 mole) 2,5-diketopiperazine was suspended in the mother liquor of example 1 by stirring. The pH was adjusted to a value of about 8 through the addition of a few drops of a 50% w/w aqueous solution of potassium carbonate. Thereupon 18 ml of formalin were added, while stirring, and the resulting suspension was heated to a temperature of 85° C. and maintained at that temperature for 1 hour.

The suspension was then further processed as in example 1 to produce 16.83 g of N,N'-dimethylol-2,5-diketopiperazine (yield=97%) with a purity of 98%.

Example 3 (Step a1)

The filtrate (=mother liquor of example 2) was further used in a subsequent synthesis of N,N'-dimethylol-2,5-diketopiperazine according to the modus operandi as in Example 2, wherein the mother liquor of example 1 was replaced by the mother liquor of example 2. N,N'-dimethylol-2,5-diketopiperazine was produced with a yield of 94% and a purity of 98%

Example 4 (Step a2)

Using the equipment of Example 1, 1.74 g (10.0 mmole) N,N'-dimethylol-2,5-diketopiperazine was suspended in 13 ml (146.9 mmole) methanesulfonic acid by stirring. Subsequently the suspension was heated to 60° C. to allow N,N'-dimethylol-2,5-diketopiperazine to dissolve in methanesulfonic acid. The solution thus obtained was cooled down, in an ice-bath, to a temperature of 0° C. Thereupon 1.14 g (5.2 mmole) tetraphosphorus hexaoxide was gradually added, while stirring, in such a way that the temperature of the reaction mixture did not exceed 60° C. The reaction mixture then was maintained at 60° C. for 16 hours and subsequently was quenched through the addition of 5 ml water. The resulting white precipitate was filtered with the aid of a Buchner funnel.

The precipitate subsequently was washed with cold water and finally dried to yield 2.48 g (8.2 mmole) pure N,N'-bisphosphonomethyl-2,5-diketopiperazine (yield=82%).

Example 5 (Step a2)

Using the equipment of Example 1, 5.23 g (30.0 mmole) N,N'-dimethylol-2,5-diketopiperazine was mixed with 16 ml (246.4 mmole) methanesulfonic acid. Subsequently, the reaction mixture was heated to 60° C. to dissolve the N,N'-dimethylol-2,5-diketopiperazine. After cooling to 0° C. 3.43 g (15.6 mmole) $P_4O_6$ was slowly added and the medium was stirred overnight at 60° C. 5 ml water was added and the resulting white precipitate was filtered off, washed with cold water and dried to yield 7.26 g of white solid consisting of 98.5% mole of N,N'-bis(phosphonomethyl)-2,5-diketopiperazine. The overall yield of N,N'-bis(phosphonomethyl)-2,5-diketopiperazine is 79.1%.

Example 6 (Step a2)

Using the equipment of Example 1, 1.74 g (10.0 mole) N,N'-dimethylol-2,5-diketopiperazine was suspended in a mixture of 10 ml 1,4-dioxane and 1.3 ml (20 mmole) methanesulfonic acid. 1.14 g (5.2 mmole) $P_4O_6$ was slowly added and the mixture was stirred overnight at 100° C. The reaction mixture medium was cooled to room temperature, 5 ml water was added and stirring was continued for 1 hour at 100° C. The obtained solution was analysed by $^{31}$P-NMR spectroscopy. N,N'-bisphosphonomethyl-2,5-diketopiperazine was detected at 13.5% mole.

Example 7 (Step a2)

Using the equipment of Example 1, 1.74 g (10.0 mmole) N,N'-dimethylol-2,5-diketopiperazine was suspended in a mixture of 15 ml acetic acid and 1.3 ml (20 mmole) methanesulfonic acid. 1.14 g (5.2 mmole) $P_4O_6$ was slowly added and the mixture was stirred overnight at 100° C. The reaction mixture was cooled to room temperature, 5 ml water was added and stirring was continued for 1 hour at 100° C. The obtained solution was analysed by $^{31}$P-NMR spectroscopy. N,N'-bisphosphonomethyl-2,5-diketopiperazine was detected at 23.0% mole.

Example 8 (Step a2)

Using the equipment of Example 1, 1.74 g (10.0 mmole) N,N'-dimethylol-2,5-diketopiperazine was suspended in 15 ml acetic acid. Then 1.14 g (5.2 mmole) $P_4O_6$ was slowly added and the mixture was stirred at 90° C. for 4 hours. The reaction mixture was cooled to room temperature and 0.9 ml (20.0 mmole) trifluoromethanesulfonic acid was added. The resulting solution was stirred for overnight at 90° C. 5 ml water was added and stirring was continued for 1 hour at 90° C. The obtained solution was analysed by $^{31}$P-NMR spectroscopy. N,N'-bisphosphonomethyl-2,5-diketopiperazine was detected at 24.6% mole.

Example 9 (Step a2)

Using the equipment of Example 1, 1.74 g (10 mmole) N,N'-dimethylol-2,5-diketopiperazine was mixed with 15 ml 1,4-dioxane under $N_2$ atmosphere. Slowly 1.14 g (5 mmole) $P_4O_6$ was added. Afterwards the reaction mixture was heated to 80° C. for 2 hours and cooled down to 40° C. 0.47 g (1 mmole) aluminium trifluoromethanesulfonate was added and the mixture was heated to 80° C. overnight. Then 2 ml water was added and the mixture was heated for 2 hours to 80° C. All volatiles were removed under vacuum and the residual solid was dissolved with water and brought to pH 5.4 by addition of sodium hydroxide. N,N'-bisphosphonomethyl-2,5-diketopiperazine was detected in 11.3% w/w, as determined by $^{31}$P-NMR spectroscopy in $H_2O/D_2O$.

Example 10 (Step a2)

Using the equipment of Example 1, 0.77 g (3.5 mmole) of $P_4O_6$ was slowly added to a mixture of 10 ml 1,4-dioxane and 0.9 ml methanesulfonic acid under $N_2$ atmosphere. Afterwards the temperature was raised to 60° C. 1.22 g (7 mmole) N,N'-dimethylol-2,5-diketopiperazine was added in small portions. Afterwards the reaction mixture was heated to 100° C. for 4 hours. After cooling to 40° C., 2 ml water was added and the mixture was heated for 2 hours to 100° C. All volatiles were removed under vacuum and the residual solid was dissolved with water and brought to pH 5.4 by addition of sodium hydroxide. N,N'-bisphosphonomethyl-2,5-diketopiperazine was detected in 14% w/w, as determined by $^{31}$P-NMR spectroscopy in $H_2O/D_2O$.

Example 11 (Step a2)

Using the equipment of Example 1, 1.22 g (7 mmole) N,N'-dimethylol-2,5-diketopiperazine was mixed with 8 ml trifluoroacetic acid and heated to 40° C. under $N_2$ atmosphere. Slowly 0.80 g (3.6 mmole) $P_4O_6$ was added. Afterwards the reaction mixture was heated to 80° C. overnight. Then 2 ml water was added and the mixture was heated for 2 hours to 80° C. The solution was diluted with water and brought to pH 5.4 by addition of sodium hydroxide. N,N'-bisphosphonomethyl-2,5-diketopiperazine was detected in 61.0% w/w, as determined by $^{31}$P-NMR spectroscopy in $H_2O/D_2O$.

Example 12 (Step a2)

Using the equipment of Example 1, 1.40 g (8 mmole) N,N'-dimethylol-2,5-diketopiperazine was mixed with 5 ml methanesulfonic acid and heated to 40° C. under $N_2$ atmosphere. Slowly 0.92 g (4.2 mmole) $P_4O_6$ was added. Afterwards the reaction mixture was heated to 80° C. overnight. Then 2 ml water was added and the mixture was heated for 2 hours to 105° C. The formed white solid was filtered off and successively rinsed with water and 2N HCl before freeze-drying. 2.06 g white solid was isolated consisting of N,N'-bisphosphonomethyl-2,5-diketopiperazine in 95% mole, as determined by $^{31}$P-NMR spectroscopy. The overall yield of N,N'-bisphosphonomethyl-2,5-diketopiperazine is 85.2%.

Example 13 (Step a2)

Using the equipment of Example 1, 4.35 g (25 mmole) N,N'-dimethylol-2,5-diketopiperazine was mixed with 13 ml methanesulfonic acid and heated to 40° C. under $N_2$ atmosphere. Slowly 2.86 g (13 mmole) $P_4O_6$ was added. Afterwards the reaction mixture was heated to 80° C. overnight. Then 2 ml water was added and the mixture was heated for 2 hours to 100° C. The formed white solid was filtered off and successively rinsed with ethanol and water before being dried. 5.6 g white solid was isolated consisting of N,N'-bisphosphonomethyl-2,5-diketopiperazine at 95% mole, as determined by $^{31}$P-NMR spectroscopy in DMSO-$d_6$. The overall yield of N,N'-bisphosphonomethyl-2,5-diketopiperazine is 74.1%.

Example 14 (Step a2)

Using the equipment of Example 1, 8.2 g (100 mmole) phosphorous acid and 0.6 ml (20.8 mmole) of $P_4O_6$ were premixed for 20 min at 85° C. Then 1.74 g (10 mmole) N,N'-dimethylol-2,5-diketopiperazine was added and the reaction mixture was heated to 85° C. overnight. Then 5 ml of water was added and the mixture was stirred at 85° C. for 1 hour. The yield of N,N'-bisphosphonomethyl-2,5-diketopiperazine in the crude reaction mixture was 0.6% mole, as determined by $^{31}$P-NMR spectroscopy.

Example 15 (Step a2)

Using the equipment of Example 1, 6 ml (92.4 mmole) of methanesulfonic acid, 1.8 g (22 mmole) of phosphorous acid and 0.3 ml (2.6 mmole) of $P_4O_6$ were premixed for 20 min at 85° C. Then 1.74 g (10 mmole) N,N'-dimethylol-2,5-diketopiperazine was added and the reaction mixture was heated to 85° C. overnight. Then 5 ml of water was added and the mixture was stirred at 85° C. for 1 hour. The yield of N,N'-bisphosphonomethyl-2,5-diketopiperazine in the crude reaction mixture was 60.7%, as determined by $^{31}$P-NMR spectroscopy.

Example 16 (Step a2)

Using the equipment of Example 1, 0.82 g (10 mmole) phosphorous acid was mixed with 5 ml (78 mmole) methanesulfonic acid. Slowly 1.37 g (10 mmole) $PCl_3$ was added, followed by 1.74 g (10 mmole) N,N'-dimethylol-2,5-diketopiperazine Afterwards the reaction mixture was stirred for 6 hours at 60° C. At ambient temperature 0.5 ml water and 20 ml acetone were added and the mixture was kept standing. After 1 hour a white solid formed that was filtered and dried. The mother liquor was kept for overnight at 4° C. causing the formation of further white solid, that was collected and dried. In total 1.4 g of the combined white solids was obtained. The solid consisted of N,N'-bisphosphonomethyl-2,5-diketopiperazine with 82% mole, as determined by $^{31}$P-NMR spectroscopy. The overall yield of N,N'-bisphosphonomethyl-2,5-diketopiperazine is 40.8%.

Example 17 (Step a2)

Using the equipment of Example 1, 1.39 g (8 mmole) N,N'-dimethylol-2,5-diketopiperazine was mixed with 5 ml (78 mmole) methanesulfonic acid. Slowly, 4.20 g (16 mmole) tetraethylpyrophosphite was added. Afterwards the reaction mixture was heated to 60° C. for 8 hours. Then 5 ml water was added and all volatiles were removed in vacuum. The residue was suspended in 10 ml acetone and the white solid was filtered off and dried to yield 1.8 g. The solid consisted of N,N'-bisphosphonomethyl-2,5-diketopiperazine with 72% mole, as determined by $^{31}$P-NMR spectroscopy. The overall yield of N,N'-bisphosphonomethyl-2,5-diketopiperazine is 66.0%.

Example 18 (Step a2)

Using the equipment of Example 1, 10 ml (154 mmole) methanesulfonic acid, 1.64 g (20 mmole) of phosphorous acid and 2.80 g (20 mmole) of $P_2O_5$ were mixed for 1 hour above 50° C. Then 1.74 g (10 mmole) N,N'-dimethylol-2,5-diketopiperazine was added and the reaction mixture was heated to 85° C. overnight. Then 6 ml of water was added and the mixture was stirred at 85° C. for 1 hour. The yield of in the crude reaction mixture was quantitative, as determined by $^{31}$P-NMR spectroscopy. The precipitated N,N'-bisphosphonomethyl-2,5-diketopiperazine was filtered off and dried. The overall yield of N,N'-bisphosphonomethyl-2,5-diketopiperazine is 2.56 g (85.0%).

Example 19 (Step a2)

Using the equipment of Example 1, 10 ml (154 mmole) methanesulfonic acid, 1.8 ml (22 mmole) of dimethylphosphite and 2.8 g (20 mmole) of $P_2O_5$ were mixed for 1 hour above 50° C. Then 1.74 g (10 mmole) N,N'-dimethylol-2,5-diketopiperazine was added and the reaction mixture was heated to 85° C. overnight. Then 6 ml of water was added and the mixture was stirred at 85° C. for 1 hour. The yield of N,N'-bisphosphonomethyl-2,5-diketopiperazine in the crude reaction mixture was 97%, as determined by $^{31}$P-NMR spectroscopy. The precipitated N,N'-bisphosphonomethyl-2,5-diketopiperazine was filtered off and dried. The overall yield of N,N'-bisphosphonomethyl-2,5-diketopiperazine is 2.53 g (84.0%).

Example 20 (Step a2)

Using the equipment of Example 1, 6 ml of methanesulfonic acid, 0.97 g (8.8 mmole) of dimethylphosphite and 0.85 g (6 mmole) of $P_2O_5$ were mixed for 20 minutes at 85° C. Then 1.74 g (10 mmole) N,N'-dimethylol-2,5-diketopiperazine was added and the reaction mixture was heated to 85° C. overnight. Then 5 ml of water was added and the mixture was stirred at 85° C. for 1 hour. The yield of N,N'-bisphosphonomethyl-2,5-diketopiperazine in the crude reaction mixture was 3.6% mole, as determined by $^{31}$P-NMR spectroscopy.

Example 21 (Step a2)

In a round-bottom flask equipped with a mechanical stirrer, a thermometer and a solid addition funnel under $N_2$ atmosphere, 4.64 g (21.1 mmole) of $P_4O_6$ were diluted in 24 ml of methanesulfonic acid under constant sonication. Gradually 6.96 g (40 mmole) N,N'-dimethylol-2,5-diketopiperazine was added to the reaction mixture over a period of 1.5 hour under constant sonication. After the addition, the sonication is kept for 1 hour and then stopped. The crude reaction mixture is reacted at room temperature for 24 hours. Then 8 ml of water was added gradually to the mixture while keeping the temperature below 40° C. The yield of N,N'-bisphosphonomethyl-2,5-diketopiperazine in the crude reaction mixture was 93% mole, as determined by $^{31}$P-NMR spectroscopy.

Example 22 (Step a1+Step a2)

In a round-bottom flask equipped with a mechanical stirrer, a thermometer and a condenser 4.52 g (40 mmole) 2,5-diketopiperazine and 2.41 g (80 mmole) paraformaldehyde were mixed with 40 ml methanesulfonic acid under $N_2$ atmosphere. The mixture was heated to 85° C. for 2 h until the solid was dissolved.

Then the mixture was cooled to 40° C. and slowly 4.40 g (20 mmole) $P_4O_6$ was added. Afterwards the reaction mixture was heated to 85° C. overnight. Then 10 ml of water was added and the mixture was heated for 2 h at 85° C. The yield of N,N'-bisphosphonomethyl-2,5-diketopiperazine in the crude reaction mixture was of 17.0%, as determined by $^{31}$P-NMR spectroscopy. The precipitated N,N'-bisphosphono-methyl-2,5-diketopiperazine was filtered off and dried. The overall yield of N,N'-bisphosphonomethyl-2,5-diketopiperazine is 0.97 g (8.0%).

Example 23 (Step b)

In a pressure-resistant sealed tube, 0.75 g (2.5 mmole) N,N'-bisphosphonomethyl-2,5-diketopiperazine was suspended in 1.35 ml of a 30% w/w aqueous HCl solution (12.41 mmole of HCl, 5 eq.). The resulting suspension was stirred for 40 hours at 120° C., which resulted in a complete dissolution of all solids. The obtained solution was analysed by $^{31}$P-NMR spectroscopy. N-(Phosphonomethyl) glycine hydrochloride was detected at 99.3% mole.

Example 24 (Step b)

In a pressure-resistant sealed tube, 0.70 g (2.3 mmole) N,N'-bisphosphonomethyl-2,5-diketopiperazine was suspended in 1.8 ml of a 36% w/w aqueous HCl solution (34.5 mmole of HCl, 15 eq.). The resulting suspension kept standing for 18 hours at 115° C., which resulted in a complete dissolution of all solids. The obtained solution was analysed by $^{31}$P-NMR spectroscopy. A complete conversion to N-(phosphonomethyl)glycine hydrochloride was observed.

Example 25 (Step b)

In a pressure-resistant sealed tube, 0.50 g (1.6 mmole) N,N'-bisphosphonomethyl-2,5-diketopiperazine was suspended in 3 ml of water along with 2 equivalents of methanesulfonic. The resulting suspension was kept standing for 20 hours at 150° C. The obtained solution was analysed by $^{31}$P-NMR spectroscopy. N-phosphonomethyl) glycine methanesulfonate was detected at 82.6% mole.

Example 26 (Step b)

In a pressure-resistant sealed tube, 0.50 g (1.6 mmole) N,N'-bisphosphonomethyl-2,5-diketopiperazine was suspended in 3 ml of water along with 2 equivalents of HCl 36% w/w. The resulting suspension was kept standing for 20 hours at 150° C. The obtained solution was analysed by $^{31}$P-NMR spectroscopy. N-(phosphonomethyl)glycine hydrochloride was detected at 84.3% mole.

Example 27 (Step b)

In a pressure-resistant sealed tube, 0.50 g (1.6 mmole) N,N'-bisphosphonomethyl-2,5-diketopiperazine was suspended in 3 ml of water along with 4 equivalents of HCl 36% w/w. The resulting suspension was kept standing for 20 hours at 165° C. The obtained solution was analysed by $^{31}$P-NMR spectroscopy. N-(phosphonomethyl)glycine hydrochloride was detected at 93.0% mole.

Example 28 (Step b)

In a pressure-resistant sealed tube, 0.50 g (1.6 mmole) N,N'-bisphosphonomethyl-2,5-diketopiperazine was suspended in 3 ml water along with 2 equivalents of sulphuric acid 98%. The resulting suspension was kept standing for 20

Example 29 (Step b)

In a pressure-resistant sealed tube, 0.50 g (1.6 mmole) N,N'-bisphosphonomethyl-2,5-diketopiperazine was suspended in 2 ml water along with 2 equivalents of sulphuric acid 98%. The resulting suspension was kept standing for 20 hours at 165° C. The obtained solution was analysed by $^{31}$P-NMR spectroscopy. N-(phosphonomethyl)glycine sulphate was detected at 93% mole.

Example 30 (Step b)

In a pressure-resistant sealed tube, 0.50 g (1.6 mmole) N,N'-bisphosphonomethyl-2,5-diketopiperazine was suspended in 3 ml water along with 4 equivalents of sulphuric acid 98%. The resulting suspension was kept standing for 20 hours at 165° C. The obtained solution was analysed by $^{31}$P-NMR spectroscopy. N-(phosphonomethyl)glycine sulphate was detected at 96.9% mole.

Example 31 (Step b)

In a pressure-resistant sealed tube, 1 g (3.2 mmole) N,N'-bisphosphonomethyl-2,5-diketopiperazine was suspended in 6 ml water. The resulting suspension was kept standing for 72 hours at 150° C. The obtained solution was analysed by $^{31}$P-NMR spectroscopy. N-(phosphonomethyl) glycine was detected at 54.9% mole.

Example 32 (Step b)

In a pressure-resistant sealed tube, 0.52 g (0.8 mmole) N,N'-bisphosphonomethyl-2,5-diketopiperazine was suspended in 3 ml water. The resulting suspension was kept standing for 25 hours at 150° C. The obtained solution was analysed by $^{31}$P-NMR spectroscopy. N-(phosphonomethyl) glycine was detected at 34.8% mole.

Example 33 (Step b)

In a pressure-resistant tube inside a Parr autoclave, 0.50 g (1.6 mmole) N,N'-bisphosphonomethyl-2,5-diketopiperazine was suspended in 3 ml water and set under a $N_2$ pressure of 1 bar. The resulting suspension was stirred for 3 hours at 240° C. The obtained solution was analysed by $^{31}$P-NMR spectroscopy. N-(phosphonomethyl)glycine was detected at 41.0% mole.

Example 34 (Step b)

The experiment was performed in a continuous process using a Vapourtec R series Flow chemistry system. A slurry of 0.25 g (0.8 mmole) N,N'-bisphosphonomethyl-2,5-diketopiperazine in water (1 ml) was loaded in the sample loop. Using water as the solvent the slurry was eluted through a High-Temperature tubing reactor (10 ml) heated to 200° C. at a flow rate of 0.1 ml·min$^{-1}$ for a period of 120 minutes. A 150 psi backpressure regulator was connected in-line between the reactor and the collection vessel from which the obtained solution was analysed by $^{31}$P-NMR spectroscopy. N-(phosphonomethyl)glycine was detected at 8.8% mole.

Example 35 (Step b)

In a pressure-resistant sealed tube, 1.0 g (3.3 mmole) N,N'-bisphosphonomethyl-2,5-diketopiperazine was suspended in 6 ml of water along with 10 equivalents of HCl 36% w/w. The resulting suspension was kept standing for 6 hours at 165° C. The excess of HCl was subsequently stripped off from the solution by distillation. 0.98 g of free glyphosate was recovered by crystallisation from the aqueous residual solution (92% isolated) with a purity of about 99%, as determined by $^{31}$P-NMR spectroscopy.

Example 36 (Step b)

In a pressure-resistant sealed tube, 1.0 g (3.3 mmole) N,N'-bisphosphonomethyl-2,5-diketopiperazine was suspended in 6 ml of water along with 6 equivalents of NaOH 50% w/w. The resulting suspension was kept standing for 6 to 7 hours at 165° C. The tri-sodium salt of glyphosate was detected in solution at 98%, as determined by $^{31}$P-NMR spectroscopy. The solution was evaporated to yield a white solid.

Example 37 (Step b)

In a pressure-resistant sealed tube, 1.0 g (3.3 mmole) N,N'-bisphosphonomethyl-2,5-diketopiperazine was suspended in 6 ml of an aqueous ammonia 29% weight (49.6 mmole). The resulting suspension was kept standing for 6 hours at 165° C.

The obtained solution was analysed by $^{31}$P-NMR spectroscopy. N-(phosphonomethyl) glycine ammonium salt was detected at 9% mole.

Example 38 (Step a2+Step b)

Using the equipment of Example 1, 1.74 g (10 mmole) N,N'-dimethylol-2,5-diketopiperazine was mixed with 6 ml methanesulfonic acid and heated to 40° C. under $N_2$ atmosphere. Slowly, 1.14 g (5.2 mmole) $P_4O_6$ was added. Afterwards the reaction mixture was heated to 70° C. for 6 hours. Then 2 ml water was added dropwise at room temperature and the obtained suspension was stored at 4° C. overnight. The resulting suspension was diluted with 9 ml of water, mixed to homogeneity and heated for 7 hours at 150° C. in a pressure-resistant sealed tube. Upon cooling, 2 ml of propanol were added and the solution was left to slowly evaporate. 0.408 g of a white-yellowish solid was isolated consisting of the mesylate salt of glyphosate in 98% mole, as determined by $^{31}$P-NMR spectroscopy.

Example 39 (Step a1+Step a2+Step b)

In a round-bottom flask equipped with a mechanical stirrer, a thermometer and a condenser 2.28 g (20 mmole) 2,5-diketopiperazine and 1.20 g (40 mmole) paraformaldehyde were mixed with 10 ml acetic acid and 1.3 ml (20 mmol) methanesulfonic acid. The mixture was heated to 80° C. for 6 hours until all solids dissolved. Then the mixture was cooled to ambient temperature and slowly 2.20 g (10 mmole) $P_4O_6$ was added. Afterwards the reaction mixture was heated for 6 hours to 80° C. Then 10 ml of water was added and the mixture was heated in a pressure tube for 8 hours at 150° C. The yield of N-(phosphonomethyl)glycine was determined by $^{31}$P-NMR spectroscopy at 11.5% w/w.

Example 40 (Step a)

Using the equipment of Example 1, 1.71 g (15 mmole) 2,5-diketopiperazine and 0.90 g (10 mmole) 1,3,5-trioxane were mixed with 10 ml methanesulfonic acid and heated to 40° C. under N$_2$ atmosphere. Then 1.65 g (0.0075 mmole) P$_4$O$_6$ was added. Afterwards the reaction mixture was heated to 80° C. overnight. Then 2 ml water was added and the obtained mixture was analysed. N,N'-bisphosphonomethyl-2,5-diketopiperazine was detected at 5.4% mole, as determined by $^{31}$P-NMR spectroscopy.

Example 41 (Step b and Formulation)

0.5 g of free glyphosate were mixed with 1 equivalent (2.95 mmole) of isopropylamine 97% in 3 ml of water and the resulting suspension was stirred at 80° C. for 30 minutes. The mono-isopropylammonium salt of glyphosate was detected at >99%, as determined by $^{31}$P-NMR spectroscopy. The solution was evaporated to yield a solid.

Example 42 (Step b and Formulation)

0.3 g of free glyphosate (1.77 mmole), suspended in 2 ml of water were successively mixed first with 3 equivalents (5.31 mmole) of NaOH 50% w/w for 10 minutes and then with 2 equivalents (3.54 mmole) of HCl 36% w/w for 10 minutes. Afterwards 1 equivalent of trimethylsulfonium iodide (1.77 mmole, 0.361 g) was added to the solution which was stirred at room temperature for 2 hours. The mono-trimethylsulfonium salt of glyphosate was detected at 99%, as determined by $^{31}$P-NMR spectroscopy. The solution was evaporated to yield a white solid.

The invention claimed is:

1. A method for the synthesis of N-(phosphonomethyl)glycine or one of its derivatives selected from the group consisting of its salts, its phosphonate esters and its phosphonate ester salts, comprising the steps of:
   a) forming, in the presence of an acid catalyst, a reaction mixture comprising 2,5-diketopiperazine, formaldehyde and a compound comprising one or more P-O-P anhydride moieties, said moieties having one P atom at the oxidation state (+III) and the other P atom at the oxidation state (+III) or (+V), to form N,N'-bisphosphonomethyl-2,5-diketopiperazine, its mono- to tetra phosphonate esters, the dehydrated forms of N,N'-bisphosphonomethyl-2,5-diketopiperazine and the phosphonate esters of its dehydrated forms; and
   b) hydrolysing said N,N'-bisphosphonomethyl-2, 5-diketopiperazine, its dehydrated forms or their phosphonate esters to obtain N-(phosphonomethyl)glycine or one of its derivatives selected from the group consisting of its salts, its phosphonate esters and its phosphonate ester salts.

2. The method according to claim 1 wherein the molar ratio of formaldehyde to 2,5-diketopiperazine is between 2 and 8.

3. The method according to claim 1 wherein the equivalent ratio of the N-H moiety of 2,5-diketopiperazine to the P-O-P anhydride moiety is between 0.2 and 2.5.

4. The method according to claim 1 wherein the ratio of moles of acid catalyst to N-H equivalents of 2,5-diketopiperazine is 2 or more.

5. The method according to claim 1 wherein the reactor content of step a) is stirred at a substantially constant temperature between 20° C. and 120° C. for a period of time between 30 minutes and 24 hours.

6. The method according to claim 1, wherein the compound comprising the P-O-P anhydride moieties is selected from the group consisting of tetraphosphorus hexaoxide, tetraethylpyrophosphite and the compounds comprising P-O-P anhydride moieties obtained from the combination of one or more compounds comprising:
   one or more P-OH moieties with one or more compounds comprising one or more P-O-P anhydride moieties or one or more P-X moieties, wherein the P atom of one or more compounds is at the oxidation state (+III);
   one or more P-X moieties and water, wherein the P atom of the P-X moiety comprising compound is at the oxidation stage (+III);
   two or more P-O-P moieties and water, wherein the P-O-P moiety comprising compound has a P atom at the oxidation state (+III) and a P atom at the oxidation state (+III) or (+V);
   wherein the compounds having one or more P-OH moieties may be accessible by tautomerization of a >P(=O)H moiety,
   wherein X is a halogenide selected from the group consisting of chlorine, bromine and iodine and
   wherein the halogen level in the P-O-P anhydride moiety comprising compound is 1000 ppm or less.

7. The method according to claim 1, wherein the compound comprising the P-O-P anhydride moieties is selected from the group consisting of tetraphosphorus hexaoxide, tetraethylpyrophosphite, and the P-O-P anhydride moiety comprising compound obtained from the combination of phosphorous acid and tetraphosphorus hexaoxide, of phosphorous acid and tetraphosphorus decaoxide, of phosphorous acid and phosphorus trichloride, of dimethylphosphite and tetraphosphorus decaoxide, of phosphorus trichloride and water and of tetraphosphorus hexaoxide and water.

8. The method according to claim 1, wherein the compound comprising the P-O-P anhydride moieties is tetraphosphorus hexaoxide.

9. The method according to claim 1 wherein step a) is divided into two separate steps comprising;
   a1) reacting 2,5-diketopiperazine with formaldehyde to form N,N'-dimethylol-2,5 diketopiperazine; and
   a2) reacting said N,N'-dimethylol-2,5-diketopiperazine with a compound comprising one or more P-O-P anhydride moieties, said moieties having one P atom at the oxidation state (+III) and the other P atom at the oxidation state (+III) or (+V), in the presence of an acid catalyst, to form N,N'-bisphosphonomethyl-2,5-diketopiperazine, its dehydrated forms or their derivatives.

10. The method according to claim 9, wherein the molar ratio of formaldehyde to 2,5-diketopiperazine is between 2.0 and 8.0.

11. The method according to claim 9, wherein 2,5-diketopiperazine is reacted with formaldehyde under aqueous alkali conditions at a pH above 7.0.

12. The method according to claim 9, wherein the step a1) of the reaction is obtained by heating at a temperature between 60° C. and 100° C. for a period of time between 20 minutes and 120 minutes.

13. The method according to claim 9, wherein N,N'-dimethylol-2,5 diketopiperazine, formed in step a1), is isolated.

14. The method according to claim 9, wherein step a2) comprises a solvent selected from the group consisting of 1,4-dioxane, toluene, ethylacetate, acetonitrile, acetic acid, sulfolane, 1-ethyl-3-methyl-imidazolium bis(trifluoromethylsulfonyl)imide, and a mixture thereof.

15. The method according to claim 9, wherein the P-O-P anhydride group comprising compound and N,N'-dimethylol-2,5-diketopiperazine, in the presence of an acid catalyst and optionally a solvent, are mixed while maintaining the reaction temperature below 120° C.

16. The method according to claim 9, wherein N,N'-dimethylol-2,5-diketopiperazine, as a solid or in solution, is added to the P-O-P anhydride moiety comprising compound comprising an acid catalyst and optionally a solvent, while maintaining the reaction temperature below 120° C.

17. The method according to claim 9, wherein the equivalent ratio of N,N'-dimethylol-2,5-diketopiperazine to the P-O-P anhydride moiety in step a2) is between 0.2 and 2.5.

18. The method according to claim 9, wherein the molar ratio of N,N'-dimethylol-2,5-diketopiperazine to tetraphosphorus hexaoxide in step a2) is between 0.5 and 5.0.

19. The method according to claim 9, wherein step a2), after completion of the addition of the P-O-P anhydride moiety comprising compound is optionally heated to a temperature between 20° C. and 120° C. and maintained at the said temperature for a period of time between 1 hour and 20 hours.

20. The method according to claim 1 comprising an additional step of isolating N,N'-bisphosphonomethyl-2,5-diketopiperazine or its derivatives.

21. The method according to claim 1 wherein the acid catalyst is a homogeneous Brønsted acid catalyst selected from the group consisting of methanesulfonic acid, trifluoromethanesulfonic acid, trifluoroacetic acid, p-toluenesulfonic acid, hydrochloric acid, phosphorous acid, phosphoric acid and mixtures thereof.

22. The method according to claim 1, wherein the acid catalyst is a heterogeneous Brønsted acid selected from the group consisting of:
(i) solid acidic metal oxide combinations as such or supported onto a carrier material;
(ii) cation exchange resins selected from the group comprising copolymers of styrene, ethylvinyl benzene and divinyl benzene, functionalized so as to graft $SO_3H$ moieties onto the aromatic group and perfluorinated resins carrying carboxylic and/or sulfonic acid groups;
(iii) organic sulfonic, carboxylic and phosphonic Brønsted acids which are substantially immiscible in the reaction medium at the reaction temperature;
(iv) an acid catalyst derived from:
the interaction of a solid support having a lone pair of electrons onto which is deposited an organic Brønsted acid; or
the interaction of a solid support having a lone pair of electrons onto which is deposited a compound having a Lewis acid site; or
heterogeneous solids functionalized by chemical grafting with a Brønsted acid group or a precursor therefore; and
(v) heterogeneous heteropolyacids of the general formula $H_xPM_yO_z$ wherein P is selected from phosphorus and silicon and M is selected from tungsten and molybdenum and combinations thereof.

23. The method according to claim 1, wherein the acid catalyst is a homogeneous Lewis acid selected from the group consisting of $LiN(CF_3SO_2)_2$, $Mg(OCF_3SO_2)_2$, $Al(OCF_3SO_2)_3$, $Bi(OCF_3SO_2)_3$, and $Sc(OCF_3SO_2)_3$.

24. The method according to claim 1, wherein the acid catalyst is a heterogeneous Lewis acid obtained from the interaction of a homogeneous Lewis acid catalyst and an organic or inorganic polymer compound.

25. The method according to claim 1, wherein the hydrolysis of step b) is performed under acid conditions, obtained from a volatile acid.

26. The method according to claim 1 wherein the acid is recovered at the end of step b) optionally purified and reused.

27. The method according to claim 1, wherein the hydrolysis of step b) is performed under alkali conditions.

28. The method according to claim 1 wherein the hydrolysis of step b) is performed under neutral conditions.

29. The method according to claim 1, wherein the hydrolysis of step b) occurs at a temperature between 25° C. and 250° C. for a period of time between 1 hour and 100 hours.

30. The method according to claim 1, wherein the derivatives are selected from the group consisting of N-(phosphonomethyl)glycine salts, phosphonate esters of N-(phosphonomethyl)glycine and phosphonate esters N-(phosphonomethyl)glycine salts and wherein the cation of the salt is selected from the group consisting of ammonium, isopropylammonium, ethanolammonium, dimethylammonium, trimethylsulfonium, sodium and potassium.

31. The method according to claim 1, wherein the N-(phosphonomethyl)glycine or its derivatives are obtained in a batch, or a continuous process.

* * * * *